(12) United States Patent
Muller et al.

(10) Patent No.: US 6,872,836 B2
(45) Date of Patent: Mar. 29, 2005

(54) PROCESS FOR THE MANUFACTURE OF 3-AMINO-PYRROLIDINE DERIVATIVES

(75) Inventors: Marc Muller, Saint-Louis (FR); Milan Soukup, Bottmingen (CH)

(73) Assignee: Basilea Pharmaceutica AG, A Swiss Company, Basel (CH)

( * ) Notice: Subject to any disclaimer, the term of this patent is extended or adjusted under 35 U.S.C. 154(b) by 0 days.

(21) Appl. No.: 10/629,483

(22) Filed: Jul. 29, 2003

(65) Prior Publication Data

US 2004/0034236 A1 Feb. 19, 2004

(30) Foreign Application Priority Data

Aug. 1, 2002 (EP) ............................................. 02016944

(51) Int. Cl.⁷ .......................................... C07D 207/04
(52) U.S. Cl. ...................................... 548/531; 548/557
(58) Field of Search ................................. 548/531, 557

(56) References Cited

U.S. PATENT DOCUMENTS 4,916,141 A * 4/1990 Sanchez ..................... 514/300

* cited by examiner

*Primary Examiner*—Rita Desai
*Assistant Examiner*—Robert Shiao
(74) *Attorney, Agent, or Firm*—Gibbons, Del Deo, Dolan, Griffinger and Vecchione

(57) ABSTRACT

The invention is concerned with a process for the manufacture of 3-amino-pyrrolidine derivatives of the formula

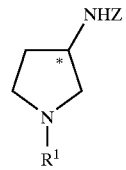

I wherein
$R^1$ signifies hydrogen or an amino protecting group;
Z signifies hydrogen or an amino protecting group; and
* represents a center of chirality. 3-Amino-pyrrolidine derivatives, especially optically active 3-amino-pyrrolidine derivatives, are intermediates for the production of agrochemicals and of pharmaceutically active substances such as, for example, of vinylpyrrolidinone-cephalosporin derivatives.

21 Claims, No Drawings

PROCESS FOR THE MANUFACTURE OF 3-AMINO-PYRROLIDINE DERIVATIVES

CROSS-REFERENCED TO THE RELATED PROVISIONAL APPLICATION

This Application claims the benefit of the European Application, Application No. 02016944.7, filed Aug. 1, 2002.

BACKGROUND OF THE INVENTION

The present invention is concerned with a novel process for the manufacture of racemic and optically active 3-amino-pyrrolidine derivatives and with the use of this process for the production of cephalosporin derivatives.

3-Amino-pyrrolidine derivatives, especially optically active 3-amino-pyrrolidine derivatives, are important intermediates for the production of agrochemicals and of pharmaceutically active substances such as, for example, of vinylpyrrolidinone-cephalosporin derivatives.

3-Amino-pyrrolidine derivatives can be manufactured in a manner known per se, for example as described in EP-A-0 218 249 starting from 1,2,4-trisubstituted butane derivatives such as e.g. tribromobutane or trihydroxybutane. The racemic derivatives can then, if desired, be converted by a racemate resolution into optically active 3-amino-pyrrolidine derivatives, as described in JP 09124595-A. A process for the manufacture of optically active 3-amino-pyrrolidine derivatives based on the conversion of 4-hydroxy-proline as described, for example, in J. Med. Chem. 1764(92), 35, gives optically active 3-aminopyrrolidine over 3 steps.

The known methods for the manufacture of 3-aminopyrrolidine derivatives as described, for example, in UK Patent No. 1,392,194, EP-A-0 391 169 and U.S. Pat. No. 4,916,141, are time consuming and lead to expensive intermediates. The interest in other processes for the manufacture of 3-amino-pyrrolidine derivatives, especially of optically active 3-amino-pyrrolidine derivatives, is therefore extremely high. Thus, Tomori et al. (Heterocycles, 1997, 1, 213–225) have synthesized (S)-3-(t-butoxycarbonylamino) pyrrolidine from (S)-3-benzyloxycarbonylamino-1,4-dimethanesulfonyloxybutane by cyclization with excess allylamine and deallylation of the resulting (S)-1-allyl-3-(benzyloxycarbonylamino)pyrrolidine with palladium on charcoal. However, on a technical scale allylamine is unpractical, being a poisonous, inflammable and explosive liquid; also, palladium is an expensive catalyst.

As can be seen, there is a need for a practical, safe, technical scale synthetic method for the synthesis of 3-aminopyrrolidine derivatives. Such a synthetic method should be cost effective and able to be performed safely on a large scale.

SUMMARY OF THE INVENTION

It was now found that 3-amino-pyrrolidine derivatives, especially optically active 3-amino-pyrrolidine derivatives, can be safely manufactured in high yield on a technical scale by replacing allylamine with hydroxylamine or its acid addition salt, particularly the hydrochloride, which is cheap and much easier to handle, having none of the disadvantages. Further, being a solid, hydroxylamine hycrochloride is easily soluble in polar organic solvents such as tetrahydrofuran, ethanol, triethylamine or mixtures thereof. The hydroxy group of the resulting N-hydroxy-3-protected-aminopyrrolidine is then removed by catalytic reduction with Raney nickel, which is a cheap catalyst.

DETAILED DESCRIPTION OF THE INVENTION

In accordance with these findings, the invention is concerned with a process for the manufacture of 3-amino-pyrrolidine derivatives of the formula

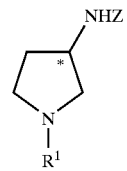

I wherein
$R^1$ signifies hydrogen or an amino protecting group;
Z signifies hydrogen or an amino protecting group; and
* represents a center of chirality,
which process comprises converting a compound of the formula

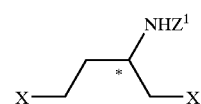

II wherein
X signifies a protected hydroxy group;
$Z^1$ signifies an amino protecting group; and
* has the above meaning,
in the presence of hydroxylamine or an acid addition salt thereof into the N-hydroxy-pyrrolidine derivative of the general formula

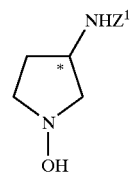

III wherein $Z^1$ and * have the above meanings,
the N-hydroxy group of which is subsequently reduced to the secondary amine of the general formula

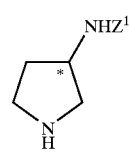

IV wherein $Z^1$ and * have the above meanings,
by hydrogenation with Raney nickel; and, if desired, protecting the secondary $N^1$ amino group by reaction with a compound of the formula $R^{10}X^1$, in which $R^{10}$ is an amino protecting group and $X^1$ is halogen or a leaving group, to yield a compound of the general formula

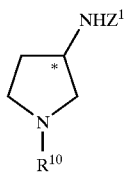

in which $R^{10}$, $Z^1$ and * have the above meanings,
and, if desired, deprotecting the secondary 3-amino group by catalytic hydrogenation to yield a compound of the general formula

VI

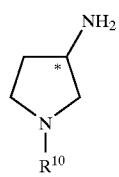

in which $R^{10}$ and * have the above meanings.

Under the above definitions the term "protected hydroxy group" in the scope of the present invention encompasses ester groups, for example, sulfonates such as mesylate, tosylate, p-bromobenzenesulphonate or p-nitrobenzenesulphonate. These are especially groups which are cleaved off selectively under the reaction conditions for the ring closure such that the amino protecting group Z in the 2-position is not liberated. Mesylate and tosylate (mesyloxy and tosyloxy) are especially preferred protected hydroxy groups X.

The term "amino protecting group" in the scope of the present invention encompasses lower alkyl, benzyl, lower alkenyl, lower alkoxycarbonyl, lower alkenyloxycarbonyl, benzyloxycarbonyl and the like. t-Butoxycarbonyl, allyloxycarbonyl and benzyloxycarbonyl, particularly the latter, are especially preferred.

The term "leaving group" embraces halogen atoms, such as chlorine or bromine, and lower alkylsulfonyloxy or lower alkylphenylsulfonyloxy groups such as mesyloxy or tosyloxy, also anhydride residues of carbonic acid such as t-butoxycarbonyloxy.

The term "lower alkyl" in the scope of the present invention encompasses straight-chain and branched, optionally chiral hydrocarbon groups with 1 to 8 carbon atoms such as, for example, methyl, ethyl, propyl, butyl, pentyl, hexyl, heptyl, octyl, i-propyl, i-butyl, tert-butyl, 2-methylbutyl and the like. "Lower alkoxy" has analogous significance.

The term "lower alkenyl" encompasses olefinic, straight chain and branched groups with 2 to 8 carbon atoms such as vinyl, allyl, 3-butenyl, 1,3-butadienyl.

The terms "lower allyl", "lower alkoxy" and "lower alkenyl" keep their meanings in combinations e.g. with "carbonyl", e.g. t-butoxycarbonyl, allyloxycarbonyl.

In an especially preferred aspect of the process of the present invention optically active R-form of 2-(benzyloxycarbonylamino)-1,4-dimethanesulfonyloxybutane is cyclized with hydroxylamine hydrochloride at about 0° C. to the boiling point of the reaction mixture in a polar solvent such as tetrahydrofuran, ethanol, triethylamine or dimethylsulfoxide or a mixture thereof, quite preferably in triethylamine. Subsequently, the hydroxy group of the resulting N-hydroxy-3-protected pyrrolidine of formula III is reductively removed by hydrogenation with Raney nickel at room temperature in a hydrogen atmosphere. The resulting secondary amine of formula IV can subsequently be N-protected, preferably by t-butoxycarbonyl, by reaction with di-t-butyl-dicarbonate, preferably at room temperature. The benzyloxycarbonyl protecting group of the resulting di-protected product of formula V is expediently removed catalytically with hydrogen and palladium on charcoal, preferably at room temperature.

The resulting primary amine of formula VI is especially suitable for manufacturing vinylpyrrolidinone-cephalosporin derivatives of the general formula

A

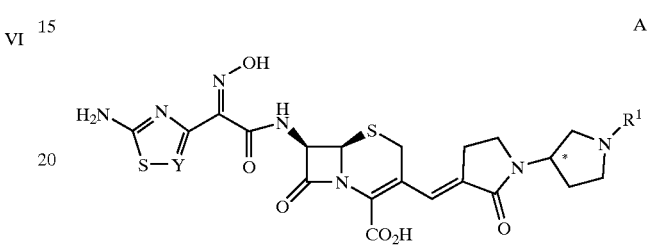

wherein
Y signifies CH or nitrogen;
$R^1$ denotes hydrogen or an amino protecting group; and
* denotes a center of chirality.

Compounds of formula A are cephalosporin derivatives having a high antibacterial activity, especially against methicillin-resistant strains of *Staphylococcus aureus* (MRSA) and *Pseudomonas aeruginosa*.

Compounds of the general formula A can be produced as per EP-A-849 269 in accordance with Scheme I:

Scheme 1

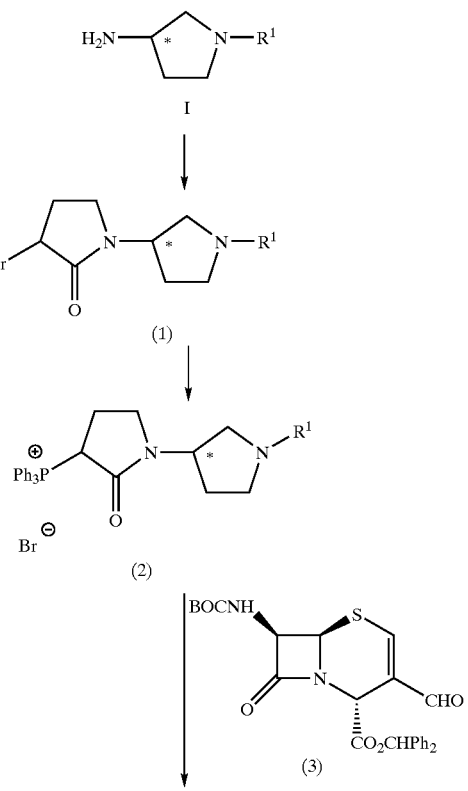

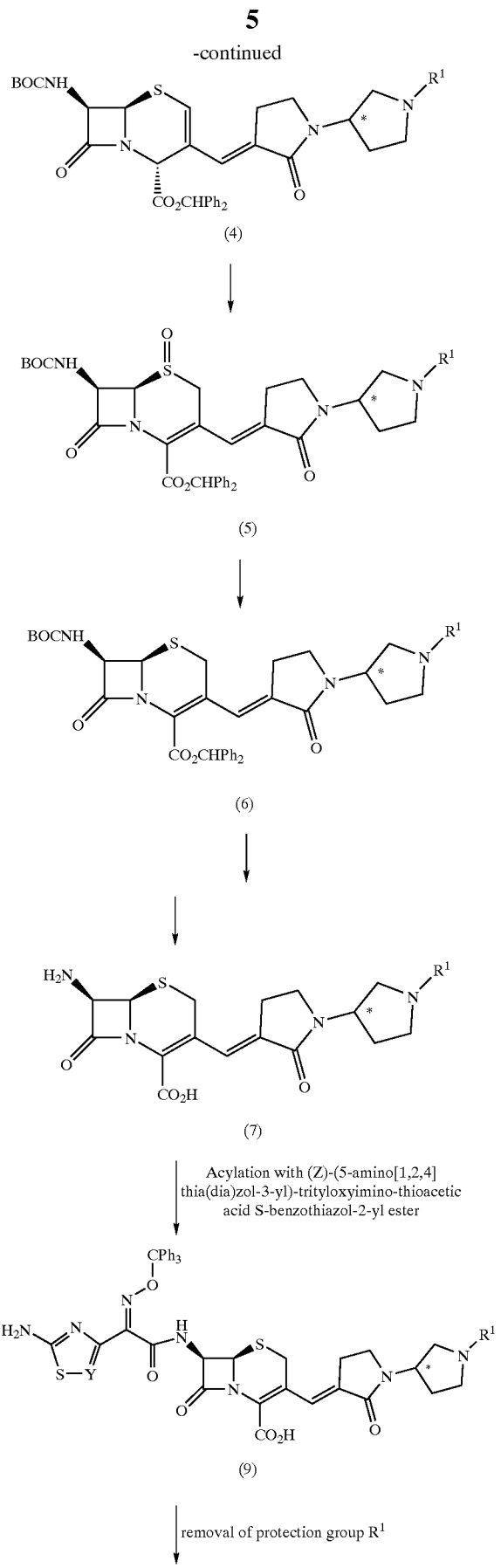

(4)

(5)

(6)

(7)

Acylation with (Z)-(5-amino[1,2,4]
thia(dia)zol-3-yl)-trityloxyimino-thioacetic
acid S-benzothiazol-2-yl ester (9)

removal of protection group $R^1$

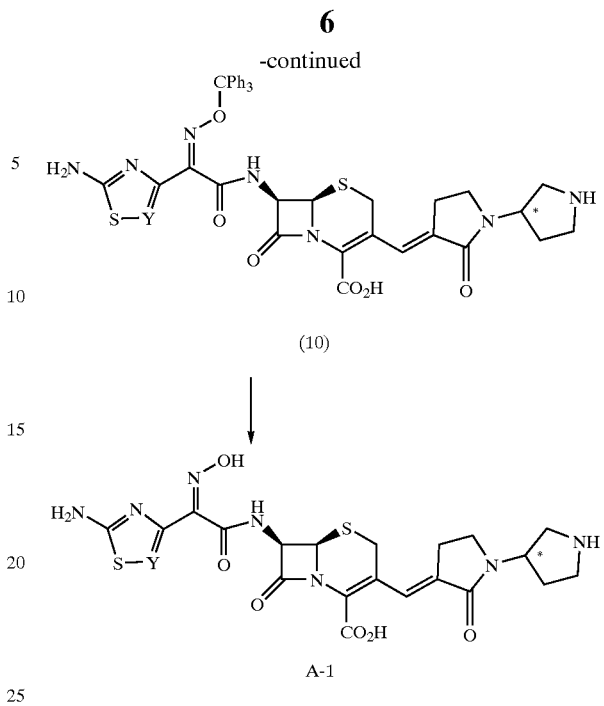

(10)

A-1

In Scheme 1 Y, $R^1$ and * have the above significance; Ph is phenyl, BOC is t-butoxycarbonyl and $CHPh_2$ is benzhydryl.

For obtaining the compounds of the general formula A the 3-amino-pyrrolidine derivative of formula I are manufactured in accordance with the invention according to the method described above, thereafter reacted in accordance with Scheme 1 with 2-bromo-4-chlorobutanoyl chloride, and the N-substituted 3-bromo-2-pyrrolidone (1) so obtained is converted into the Wittig salt (2) which is reacted with the diprotected 3-ene cephalosporin (3). The resulting condensation product (4) is oxidized to the 5-sulfoxide (5) which is reductively isomerized with $PBr_3$ to the 2-ene cephalosporin (6), the latter is N-deprotected and acylated with the activated acyl derivative (8) to yield (9) which is deprotected in two steps to yield (10) and finally the end product of formula A.

The following Examples serve to illustrate the invention.

EXAMPLE 1

(R)-3-(Benzyloxycarbonylamino)-N-hydroxy-pyrrolidine (R)-2-(Benzyloxycarbonylamino)-1,4-dimethanesulfonyloxybutane (2.0 g; 5.06 mmol) was dissolved in a $Et_3N/DMSO$ mixture (1:1, 20 ml). Hydroxylamine hydrochloride (1.4 g; 20.2 mmol) was added and the mixture was heated at 60° C. over night. The mixture was poured in aqueous HCl (the pH was adjusted to pH=6 with $NaHCO_3$) and extracted twice with AcOEt. The organic phase was washed with water and dried over $Na_2SO_4$. The solids were filtered off and the solvent was removed. A light yellow oil (1.4 g, purity 73%) was obtained (yield: 85%). The crude title compound was used as is.

EXAMPLE 2

(R)-3-(Benzyloxycarbonylamino)-N-(t-butoxycarbonyl)-pyrrolidine

The crude (R)-3-(benzyloxycarbonylamino)-N-hydroxypyrrolidine obtained above (1.4 g) was dissolved in ethanol (10 ml). Raney nickel (about 2 g) was added to this mixture. The reaction was degassed under reduced pressure and hydrogen supply (three times) and subsequently put under hydrogen atmosphere (1 bar). The reaction was over after 6 hours, yielding crude (R)-3-(benzyloxycarbonylamino)-pyrrolidine which was further processed in situ, in that di-tert-butyl dicarbonate (1.0 g, 4.58 mmol) was added; the mixture was stirred for one hour. The solvent was removed and the residue taken up in an n-hexane/AcOEt mixture (1:1, 20 ml) and filtered through a silicagel pad. The silica was washed with n-hexane/AcOEt mixture (1:1; 250 ml). The organic phases were evaporated. The compound was obtained as a colorless oil (1.125 g; yield 81%) in good purity, i.e. at least 90–95%, rendering the compound sufficiently pure for further reaction, e.g. in Example 3.

NMR: (CDCl$_3$; 300 MHz): 7.34 (m;5H); 5.1 (s(broad); 2H; 4.83 (m(broad); 1H); 4.22 (m(broad); 1H); 3.60 (dd; 1H); 3.41 (m(broad); 2H); 3.18 (m(broad); 1H); 2.12 (m; 1H); 1.82 (m(broad); 1H); 1.45 (s; 9H).

MS: (M+H$^+$): 321.3 (M+NH$_4^+$): 338.2

Example 2 may also be carried out under pressure in a pressure reactor at a pressure range of 1 to 50 kg, more preferred 1 to 20 kg, most preferred at a pressure of 3.8 kg. Further the reaction may be carried out at a temperature between 20° C. and 100° C., more preferred 40° C. to 60° C., most preferred the reaction may be carried out at a temperature of 55° C.

EXAMPLE 3

(R)-3-Amino-N-(t-butoxycarbonyl)-pyrrolidine (R)-3-(Benzyloxycarbonylamino)-N-(t-butoxycarbonyl)-pyrrolidine (300 mg) was dissolved in ethanol (5 ml). Palladium on charcoal 10% (20 mg) was added. The reaction was degassed three times and put under hydrogen atmosphere (1 bar). The reaction was over after 2 hours. The solvent was removed, the residue was taken up in ethyl acetate (5 ml) and filtered through a silica gel pad. The silica was washed with ethyl acetate (50 ml). The organic phases were evaporated. The desired (R)-3-Amino-N-(t-butoxycarbonyl)-pyrrolidine was obtained as a colorless oil in a quantitative yield (175 mg).

NMR: (CDCl$_3$; 300 MHz): 3.6–3.3 (m(broad); 3H); 3.05 (m(broad); 1H); 2.29 (s(broad); 2H); 2.05 (m; 1H); 1.66 (m(broad); 1H); 1.46 (s; 9H).

MS: (M+H$^+$): 187.3

Example 3 may also be carried out under pressure in a pressure reactor at a pressure range of 1 to 50 kg, more preferred 5 to 40 kg, most preferred at a pressure of 20 kg. Further the reaction may be carried out in the presence of an acid (after the addition of Pd/C), such as acetic acid, HCl or perchloric acid. Most preferred perchloric acid is used.

The (R)-3-amino-N-(t-butoxycarbonyl)-pyrrolidine can be utilized in Example 2 of EP-A-0 849 269 instead of the N-allyloxycarbonyl derivative and subsequently in Examples 3–11 to yield (6R,7R)-7-[(Z)-2-(5-amino-[1,2,4] thiadiaol-3-yl)-2-hydroxyimino-acetylamino]-8-oxo-3-[(E)-(R)-2-oxo-[1,3']bipyrrolidinyl-3-ylidenemethyl]-5-thia-1-aza-bicyclo[4.2.0]oct-2-ene-2-carboxylic acid of the formula

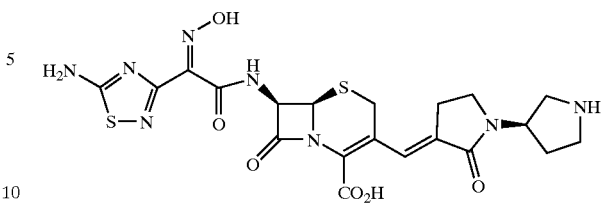

A-1

EXAMPLE 4

A 200 l reactor was charged with 27 l of dimethylsulfoxide, 9.5 kg of (R)-2-(benzyloxycarbonylamino)-1,4-dimethanesulfonyloxybutane and 6.68 kg of hydroxylamine hydrochloride and the reaction mixture stirred at room temperature to suspend. 27 l of triethylamine were added slowly, whereupon the temperature rose to 45–50° C. The reaction mass was maintained at 55° C. for four hours. The reaction was monitored by NMR or HPLC (high performance liquid chromatography). Subsequently the reaction mixture was cooled to room temperature.

Separately a solution was prepared with 100 l of water at 0° C. containing 14.2 l of concentrated aqueous hydrochloric acid. The above reaction mass was added to this solution and the pH value checked to 1.0 to 1.5. The aqueous layer was washed twice with each 10 l of 1:1 ethyl acetate and n-hexane and neutralized with 15 kg of sodium bicarbonate. The reaction mixture was stirred for 30 minutes and the pH checked to about 7.0–7.5. The aqueous layer was extracted three times with 15 l of ethyl acetate each time. The combined organic phases were washed twice with each 15 l of water followed by 10 l of brine (saturated aqueous sodium chloride solution).

The solvent was evaporated at reduced pressure, at the end of which the oily residue was stripped with 10 l of n-hexane. The n-hexane was evaporated off, n-hexane added again and the mixture stirred to precipitate the product. The crude (R)-3-(Benzyloxycarbonylamino)-N-hydroxy-pyrrolidine was filtered off and used directly in example 5. The white solid obtained changed to yellow upon storage.

Yield 4.6–5.0 kg (80–85%) having a purity of more than 95%.

EXAMPLE 5

A 50 l autoclave was charged with 22.5 l of ethanol, 4.5 kg of (R)-3-(benzyloxycarbonylamino)-N-hydroxy-pyrrolidine and 1.35 kg of Raney nickel. The autoclave was put under hydrogen atmosphere (50 psi=3.5 bar) and stirred for four hours. The reaction was monitored by HPLC and TLC.

After reaction the catalyst was filtered off and the solvent removed by evaporation at reduced pressure. The residue, crude (R)-3-(benzyloxycarbonylamino)-pyrrolidine, was dissolved in 20 l of ethanol followed by 4.15 kg of di-tert-butyl dicarbonate. The reaction mixture was stirred at room temperature for two hours, the reaction being monitored by HPLC and TLC. The solvent was evaporated off at reduced pressure, the reaction mixture being stripped twice by the addition of 2 l of toluene each time.

5.7 kg of crude (R)-3-(benzyloxycarbonylamino)-N-(t-butoxycarbonyl)-pyrrolidine was obtained as a yellowish oily residue, which was purified by dissolution, in a 20 l reactor, in 11.4 l of methylene chloride followed by 2.85 kg of silica gel and 57 g of charcoal. The reaction mixture was stirred for two hours at room temperature. The solids were filtered off and washed thoroughly with 10 l of methylene chloride. The combined organic layers were evaporated at reduced pressure, yielding 5.1 kg of (R)-3-(benzyloxycarbonylamino)-N-(t-butoxycarbonyl)-pyrrolidine as a colorless oil.

EXAMPLE 6

An autoclave was charged with 51 l of ethanol, 5.1 kg of (R)-3-(benzyloxycarbonylamino)-N-(t-butoxycarbonyl)-pyrrolidine, 0.51 g of 5% palladium-on-carbon and 0.5 l of perchloric acid. The autoclave was put under hydrogen atmosphere (100 psi=7 bar) for one hour, the reaction being monitored by NMR. After completion of the reaction the catalyst was filtered off and the solvent removed under reduced pressure.

The oily residue was dissolved in 10 l of ethyl acetate and the organic layer washed with 10 l of water, followed by 10 l 10% aqueous sodium carbonate solution. The organic phase was dried over sodium sulfate and the solvent removed by evaporation under reduced pressure. 2.5 kg of (R)-3-Amino-N-(t-butoxycarbonyl)-pyrrolidine was obtained as a colorless oil.

The NMR spectrum is identical with that reported under Example 3.

All references discussed throughout the above specification are herein incorporated in their entirety by reference for the subject matter they contain.

It should be understood, of course, that the foregoing relates to preferred embodiments of the invention and that modifications may be made without departing from the spirit and scope of the invention as set forth in the following claims.

What is claimed is:

1. A process for the manufacture of 3-protected amino-pyrrolidine derivatives of the formula

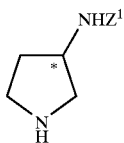

wherein;
Z$^1$ is an amino protecting group; and
* is a center of chirality,
which process comprises:
converting a compound of the formula

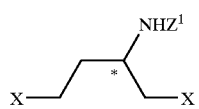

wherein
X is a protected hydroxy group; and
Z$^1$ is an amino protecting group; and
* is a center of chirality, by reaction with hydroxylamine or an acid addition salt thereof into a N-hydroxy-3-protected amino pyrrolidine derivative of the formula

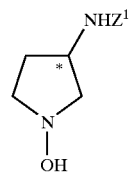

wherein
Z$^1$ is an amino protecting group; and
* is a center of chirality, reducing by hydrogenation with Raney nickel, the N-hydroxy group in the compound of formula III to produce said 3-protected amino-pyrrolidine derivative of formula IV.

2. The process according to claim 1, wherein the center of chirality is in the R-form.

3. The process according to claim 1, wherein X is mesyloxy.

4. The process according to claim 1, wherein Z$^1$ is benzyloxycarbonyl.

5. The process according to claim 1, wherein the compound of formula II is reacted with hydroxylamine hydrochloride.

6. The process according to claim 1, wherein each step is carried out under pressure.

7. A process for the manufacture of a di-protected 3-protected amino-pyrrolidine of the formula:

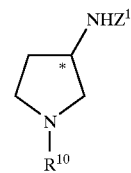

wherein;
Z$^1$ and R$^{10}$ are amino protecting groups;
Z$^1$ is an amino protecting group; and
* is a center of chirality, which process comprises:

converting a compound of the formula

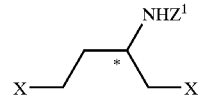

wherein
X is a protected hydroxy group; and
Z$^1$ is an amino protecting group; and
* is a center of chirality, by reaction with hydroxylamine or an acid addition salt thereof into a N-hydroxy-3-protected amino pyrrolidine derivative of the formula

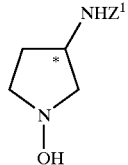

III wherein;
$Z^1$ is an amino protecting group; and
* is a center of chirality, reducing by hydrogenation with Raney nickel the N-hydroxy group in the compound of formula III to produce the N-amino 3-protected amino pyrrolidine derivative of the formula

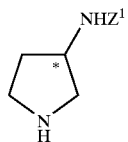

IV wherein;
$Z^1$ is an amino protecting group; and
* is a center of chirality, and reacting the compound of formula IV with a compound of the formula $R^{10}X^1$, in which $R^{10}$ is an amino protecting group and $X^1$ is halogen or a leaving group, to protect the N-amino group in the compound of formula IV and produce said di-protected 3-amino-pyrrolidine of the formula V.

8. The process of claim 7, wherein the center of chirality is in the R-form.

9. The process of claim 7, wherein X is mesyloxy.

10. The process of claim 7, wherein $Z^1$ is benzyloxycarbonyl.

11. The process of claim 7, wherein the compound of formula II is reacted with hydroxylamine hydrochloride.

12. The process of claim 7 wherein said compound $R^{10}X^1$ is di-tert-butyl-dicarbonate.

13. The process of claim 7 wherein each step is carried out under pressure.

14. A process for the production of a N-protected amino 3-amino pyrrolidine derivatives of the formula

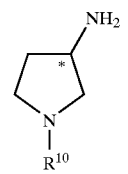

VI wherein
$R^{10}$ is amino protecting group; and
* is a center of chirality, which process comprises:
converting a compound of the formula

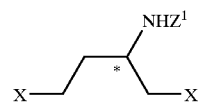

II wherein
X is a protected hydroxy group; and
$Z^1$ is an amino protecting group; and
* is a center of chirality, by reacting with hydroxylamine or an acid addition salt thereof into a N-hydroxy-3 amino protected pyrrolidine derivative of the formula

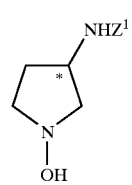

III wherein;
$Z^1$ is an amino protecting group; and
* is a center of chirality, reducing by hydrogenation with Raney nickel, the N-hydroxy group in the compound of formula III to produce the N-amino-3-amino pyrrolidine derivative of the formula

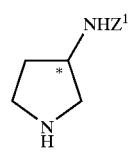

IV wherein;
$Z^1$ is an amino protecting group; and
* is a center of chirality, and reacting the compound of formula IV with a compound of the formula $R^{10}X^1$, in which $R^{10}$ is an amino protecting group and $X^1$ is a halogen or a leaving group, to protect N amino group in the compound of formula IV, to produce a protected an N protected 3-protected amino pyrrolidine derivative of the formula:

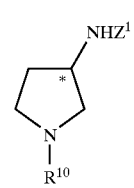

V wherein;
$R^{10}$ is amino protecting group; and
$Z^1$ is an amino protecting group; and
* is a center of chirality, and thereafter selectively deprotecting 3-amino group in the compound of Formula V, by catalytic hydrogenation to produce said N-protected amino-pyrrolidine derivative of formula VI.

15. The process of claim 14, wherein the center of chirality is in the R-form.

16. The process of claim 14, wherein X is mesyloxy.

17. The process of claim 14, wherein $Z^1$ is benzyloxycarbonyl.

18. the process of claim 14, wherein the compound of Formula II is reacted with hydroxylamine hydrochloride.

19. The process of claim 14, wherein the compound $R^{10}X^1$ is di-tert-butyl-dicarbonate.

20. The process of claim 14, wherein the selected deprotection of the compound of formula V is carried out by catalytic hydrogenation with palladium on charcoal.

21. The process according to claim 14, wherein each step is carried out under pressure.

* * * * *